United States Patent
Landgrebe et al.

(10) Patent No.: US 6,432,396 B1
(45) Date of Patent: Aug. 13, 2002

(54) LIMITING THE PRESENCE OF MICROORGANISMS USING POLYMER-BOUND METAL-CONTAINING COMPOSITIONS

(75) Inventors: Kevin D. Landgrebe, Woodbury, MN (US); David J. Hastings, London (CA); Terrance P. Smith, Woodbury, MN (US); Gregory D. Cuny, Hudson, MA (US); Ashok Sengupta, London (CA); Chandrika D. Mudalige, London (CA); Frank A. Brandys, London (CA)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/611,346

(22) Filed: Jul. 6, 2000

(51) Int. Cl.[7] .................. A61K 31/74; A61K 31/555; A01N 55/05; C07D 229/00; C07D 205/12
(52) U.S. Cl. ............... 424/78.08; 424/406; 514/184; 540/202; 540/203
(58) Field of Search ..................... 424/78.08, 406; 514/184; 540/202, 203

(56) References Cited

U.S. PATENT DOCUMENTS

| | | |
|---|---|---|
| 4,539,256 A | 9/1985 | Shipman |
| 4,775,625 A | 10/1988 | Sieber |
| 4,885,366 A | 12/1989 | Gunther et al. |
| 4,906,750 A | 3/1990 | Gunther et al. |
| 4,915,683 A | 4/1990 | Sieber |
| 4,937,344 A | 6/1990 | Gunther et al. |
| 5,149,718 A | 9/1992 | Meruelo et al. |
| 5,166,326 A * | 11/1992 | Smith et al. ............... 534/701 |
| 5,180,705 A | 1/1993 | Smith |
| 5,208,336 A | 5/1993 | Gunther et al. |
| 5,314,998 A | 5/1994 | Smith |
| 5,326,788 A | 7/1994 | Meruelo et al. |
| 5,418,130 A | 5/1995 | Platz et al. |
| 5,461,155 A | 10/1995 | Smith |
| 5,571,666 A | 11/1996 | Floyd et al. |
| 5,585,407 A | 12/1996 | Patel |
| 5,650,441 A | 7/1997 | Aszalos et al. |
| 5,830,526 A | 11/1998 | Wilson |
| 6,248,733 B1 * | 6/2001 | Landgrebe et al. ......... 514/184 |

FOREIGN PATENT DOCUMENTS

| | | |
|---|---|---|
| EP | 0 457 196 | 11/1991 |
| EP | 0 503 780 | 9/1992 |
| EP | 0 508 573 | 10/1992 |
| EP | 0 591 016 | 4/1994 |
| JP | 05 170646 | 7/1993 |
| SU | 486 68 | 4/1976 |

(List continued on next page.)

OTHER PUBLICATIONS

Abildgaard et al., "Assignment of the Ligating Nitrogen in o,o'–Dihydroxylazorarene Complexes of Nickel–, Palladium and Platinum(ii) by $^1$H and $^{13}$C NMR Spectroscopy," *Inorganic Chemistry*, vol. 33, No. 23, pp. 5271–5277 (1994).

(List continued on next page.)

Primary Examiner—Thurman K. Page
Assistant Examiner—Blessing Fubara
(74) Attorney, Agent, or Firm—Paul W. Busse; Christopher D. Gram; Robert W. Sprague

(57) ABSTRACT

The present invention provides a method of limiting the presence of a microorganism by contacting the microorganism with polymer-bound metal-containing compositions. The compositions include metal-containing compounds that may be prepared by reacting or polymerizing metal-containing monomers. The microorganism may be present in a liquid that is contacted with the polymer-bound metal-containing composition. Alternatively, the microorganism may be present in a solid that is contacted with the polymer-bound metal-containing composition.

29 Claims, 2 Drawing Sheets

FOREIGN PATENT DOCUMENTS

| | | |
|---|---|---|
| SU | 401 169 | 5/1976 |
| WO | WO 90/13296 | 11/1990 |
| WO | WO-92/22610 | * 12/1992 |
| WO | WO 93/00815 | 1/1993 |
| WO | WO 95/02325 | 1/1995 |
| WO | WO 95/16348 | 6/1995 |
| WO | WO 98/03224 | 1/1998 |
| WO | WO 98/20904 | 5/1998 |
| WO | WO-99/37154 | * 7/1999 |
| WO | WO 00/78854 A1 | 12/2000 |

OTHER PUBLICATIONS

M. Bhatti et al., "An Investigation Into the Mechanisms Involved In, and Possible Targets of, Lethal Photosensitisation of Porphyromonas Gingivalis", Abstract No. B–94, Interscience Conference on Antimicrobial Agents & Chemotherapy, Sep. 28–Oct. 1, 1997, Toronto, Ontario, Canada, 1 page.

S. Gaspard et al., "Studies on photoinactivation by various phthalocyanines of a free or replicating non–enveloped virus," *Journal of Photochemistry and Photobiology B: Biology* 31, pp. 159–162 (1995).

Gupta et al., Spectral, Microbial Studies, *Proceedings of the National Academy of Science*, India, Sect. A, 61(3), Abstract, 1 page.

B. Henderson et al., Photodynamic Therapy: Basic Principles and Clinical Applications, Title page, Publication page, and p. 98 (1992).

Jackson et al., "Killing of Candida Albicans by Antibody–targeted photolysis," Abstract No. F–104, Interscience Conference on Antimicrobial Agents & Chemotherapy, Sep. 28–Oct. 1, 1997, Toronto, Ontario, Canada, 1 page.

Motschi et al., *Helvetica Chimica Acta*, 63(7): 2071–2086 (1980).

H. Okamoto et al., "Dye–Mediated Bacterial Effect of He–Ne Laser Irradiation on Oral Microorganisms," *Lasers in Surgery and Medicine*, vol. 12, pp. 450–458 (1992).

R. Pal et al., "Effect of Evans Blue and Trypan Blue on Syncytia Formation and Inefectivity of Human Immunodeficiency Virus Type I and Type II In Vitro," *AIDS Research and Human Retroviruses*, vol. 7, No. 6, pp. 537–543 (1991).

Wade, *Organic Chemistry* ($3^{rd}$ Edition), Chapter 16, pp. 730–732, Prentice Hall Inc., (1995).

Bezman et al., "Photodynamic Inactivation of E. Coli By Rose Bengal Immobilized On Polystyrene Beads," *Photochemistry and Photobiology*, vol. 28, pp. 325–329 (1978).

Bonnett et al., "Immobilized photosensitizers: photosensitizer films with microbicidal effects," *SPIE*, vol. 3191, pp. 79–88 (1997).

Dahl et al., "Pure Singlet Oxygen Cytotoxicity For Bacteria," *Photochemistry and Photobiology*, vol. 46, No. 3, pp. 345–352 (1987).

Gupta et al., "Studies On Polynucleotides, LXXXVII.* The Joining of Short Deoxyribopolynucleotides By DNA–Joining Enzymes," *Proceedings of the National Academy of Sciences of the United States of America*, vol. 60, pp. 285–292 (1968).

Minnock et al., "Photoinactivation of bacteria. Use of a cationic water–soluble zinc phthalocyanine to photoinactivate both Gram–negative and Gram–positive bacteria," *Journal of Photochemistry and Photobiology B: Biology* 32, pp. 159–164 (1996).

* cited by examiner

LIMITING THE PRESENCE OF MICROORGANISMS USING POLYMER-BOUND METAL-CONTAINING COMPOSITIONS

FIELD OF THE INVENTION

This invention relates to polymer-bound metal-containing compositions, and the use of such compositions to limit the growth of viruses, bacteria, and fungi.

BACKGROUND OF THE INVENTION

The potential for the presence of pathogenic bacteria and viruses in biological fluids such as saliva, tears, blood, and lymph is of significant concern as is the potential for the transfer of such microorganisms to the surfaces of medical devices (and vice versa). For these reasons, methods for minimizing the transmission of pathogens in the home and in hospitals, as well as in day-care centers, are important.

Microorganisms can be killed or rendered static by a number of physical and chemical methods. Physical methods include heat and radiation. There are a number of chemicals that have been used to limit viral, fungal, and bacterial growth. Examples include alcohols (usually, 70% by volume aqueous ethyl or isopropyl alcohol); phenol and phenol derivatives such as hexachlorophene; formaldehyde; glutaraldehyde; ethylene oxide; ether; detergents; chlorhexidine gluconate; heavy metals such as silver, copper, and mercury; organic compounds of mercury such as mercurochrome; as well as oxidizing agents such as hydrogen peroxide, iodine, hypochlorite, and chlorine.

Antibiotics, such as bacitracin, the cephalosporins, cycloserine, the penicillins, vancomycin, chloramphenicol, the erythromycins, the tetracyclines, the sulfonamides, and the aminoglycosides (such as streptomycin, neomycin, and gentamycin) have traditionally been defined as chemicals made by microorganisms that kill bacteria. Antibiotics have no effect on viruses.

Many of such treatment methods are neither permanent nor continuous. Thus, repeated treatments may be needed to restore sterility during and after use. Polymeric compositions intended for imparting a continuously antimicrobial, self-disinfecting property to surfaces or liquids are known. Typically, these involve an antimicrobial agent and a polymer in a mixture that allows leaching of the antimicrobial agent for controlled release. In some cases, the antimicrobial agent that leaches from the polymer is toxic or imparts undesirable properties to the material in the leached form. Thus, there is considerable interest in autosterile (possessing intrinsic microbicidal activity) non-leaching materials.

There are also examples of polymeric compositions that include an antimicrobial moiety covalently bonded to a polymer. Rose bengal, for example, has been covalently attached to poly(styrene), and porphyrins have been bonded to acrylates, with the resulting polymers in both cases possessing antimicrobial activity with no leaching.

Singlet oxygen is generated in neutrophils and macrophages for use in killing microorganisms of a wide variety. The "photodynamic effect" is the term used to describe destruction of cells and microbes by triplet-sensitizers in the presence of oxygen and light. Singlet oxygen is believed to be the destructive agent under conditions where oxygen concentration is high and there are no reducing agents present. Singlet oxygen is a short-lived excited state of molecular oxygen. In solution, its lifetime of 1 microsecond allows it to diffuse on the order of 0.1 micron before being deactivated to triplet molecular oxygen. In the gas phase in air, the lifetime of singlet oxygen is about 1 millisecond, which allows for diffusion of up to 1 millimeter before deactivation to triplet oxygen. The combinations of certain photosensitizers, oxygen, and light have been shown to be toxic to living tissue, which is believed to be the consequence of the formation of singlet oxygen.

Thus, photosensitizing dyes, such as merocyanines and water-soluble zinc phthalocyanines, have been disclosed for use as antimicrobial agents. Surfaces coated with certain photosensitizers can be made to be autosterile. Due to the catalytic nature of the photosensitizer-oxygen reaction that generates singlet oxygen and regenerates ground-state photosensitizers, the antimicrobial activity of such coatings can be made to be essentially permanent. Additionally, certain immobilized photosensitizers have been shown to exhibit antimicrobial activity at a distance due to diffusion of singlet oxygen.

Use of photosensitizers compounded with or covalently attached to polymers to prepare substantially non-leaching autosterile materials is known. For example, various polymers that include covalently-bound porphyrin, phthalocyanine, and Rose Bengal photosensitizers are known.

U.S. Pat. No. 6,248,733 (Landgrebe et al.) discloses the use of metal-containing compounds in polymeric compositions (e.g., porous fabrics). For certain embodiments of the compounds described therein, specifically, wherein $R_1$ includes a long chain organic group containing, e.g., 8 or 9 carbon atoms, no antimicrobial activity was observed. These findings are consistent with the theory that leaching of the metal-containing compound is required to impart antimicrobial activity.

SUMMARY OF THE INVENTION

In one aspect, the present invention provides a method for limiting the presence of a microorganism. The method includes contacting the microorganism with a polymer-bound metal-containing composition. The composition includes a compound having the following formula:

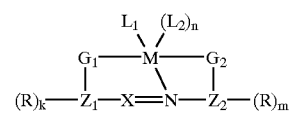

wherein:

$Z_1$ and $Z_2$ each independently represent an arene nucleus, which has from 5 to 14 ring atoms;

$G_1$ and $G_2$ each independently represent a metal ligating group such that $G_1$ and $G_2$ may be contained within or pendant from at least one of $Z_1$ and $Z_2$;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkyl- or aryl sulfonyl group, an alkyl- or aryl sulfoxyl group, an aryloxyl group, a hydroxyl group, a thioamido, a carbamoyl group, a sulfamoyl group, a formyl group, an acyl group, a ureido group, an aryloxycarbonyl group, a silyl group, or a sulfoalkoxy group;

$L_1$ represents a nitrogen heterocycle substituted with $R_1$ or $R_2$ or both $R_1$ and $R_2$;

$R_1$ and $R_2$ each independently represent a polymer-bound group, a hydrogen, a halogen atom, an alkyl group, a vinyl group, a hydroxyalkyl group, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group; wherein at least one of $R_1$ and $R_2$ represents a polymer-bound group;

$L_2$ represents a monodentate or polydentate ligand;

X represents nitrogen or a methine group;

M represents a platinum or palladium atom; and k, m, and n are whole numbers less than or equal to 4.

In one embodiment, the polymer-bound metal-containing composition includes a compound of the following formula:

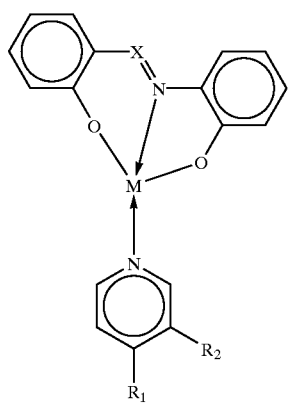

wherein:

$R_1$ and $R_2$ each independently represent H or a polymer-bound group, wherein at least one of $R_1$ and $R_2$ is a polymer-bound group; X represents nitrogen or a methine group; and M represents a platinum or palladium atom.

In another aspect, the present invention provides a polymer-bound metal-containing compound of the following formula:

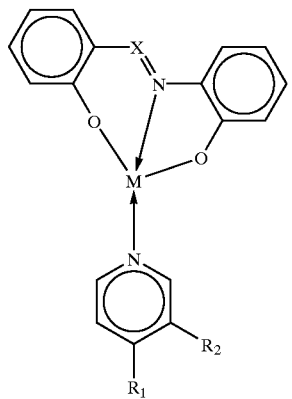

wherein:

$R_1$ and $R_2$ each independently represent H or a polyurethane-bound group, wherein at least one of $R_1$ and $R_2$ represents a polyurethane-bound group;

X represents nitrogen or a methine group; and

M represents a platinum or palladium atom.

In still another aspect, the present invention provides a method of preparing a polymer-bound metal-containing compound that includes reacting a prepolymer or polymer with a metal-containing monomer of the following formula:

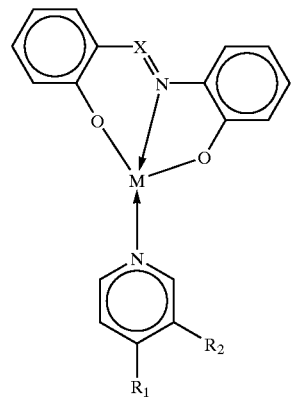

wherein:

$R_1$ and $R_2$ each independently represent H or $CH_2OH$, wherein at least one of $R_1$ and $R_2$ represents $CH_2OH$;

X represents nitrogen or a methine group; and

M represents a platinum or palladium atom.

In one embodiment, the method includes reacting an isocyanate functional prepolymer or polymer with the monomer.

DEFINITIONS

"Polymer-bound" means a group that is irreversibly attached to a polymer either through covalent bonds or steric entanglement. A polymer-bound group that is a substituent on a heterocyclic ring may be a polymer that is covalently attached to the heterocyclic ring either through a backbone atom, a side chain atom, or a terminal atom of a polymer chain. Alternatively, the polymer-bound group may be a group that is sterically entangled with a polymer chain, such as might arise by dimerization, oligomerization, or polymerization of a reactive group attached to the heterocyclic ring in the presence of a preformed polymeric matrix. Preferably, the polymer-bound group includes a polymer covalently attached to the heterocyclic ring. "Metal-containing compound" means that the compound contains one or more coordinated transition metal atom, preferably platinum or palladium.

For the purposes of this invention, the terms "limiting the presence of a microorganism" or "antimicrobial activity" include limiting the presence of at least one virus, at least one bacterium, at least one fungus, or a combination thereof. Limiting the presence of a microorganism includes limiting the growth of a microorganism. This term also includes inhibiting, inactivating, killing, or preventing the replication of or reducing the number of microorganisms. Different terms may be used for different microorganisms.

The terms "limiting the presence of a virus," "inactivation of virus," "viricidal activity," and "viricidal" as used herein refer to a reduction in the amount of virus present in a sample contacted with the composition of the present invention. These terms also refer to a reduction in the amount of virus, present in a sample contacted with the composition of this invention, that is able to enter and/or replicate in a cell. Preferably, the terms refer to at least about 50% reduction in the amount of at least one species of virus detected on a surface of the composition relative to similar compositions that do not include metal-containing compounds under the same conditions, using the test method as described in Example 4 below. More preferably, the compositions of the present invention provide at least about 75% reduction in the amount of at least one species of virus, even more preferably, at least about 90% reduction, and most preferably, at least about 99% reduction in at least one species of virus.

The term "limiting the presence of a fungus or a bacterium" as used herein refers to methods that employ the use of compositions of the present invention to inhibit, kill, or prevent the replication of or reduce the number of bacteria or fungi present on a surface of the composition. Preferably, the term refers to an at least about 40% reduction (as evidenced by the inhibition of growth or killing, for example) in the amount of at least one species of fungus or bacterium detected on a surface under the same conditions using the test method described in Example 5, for a composition of the present invention relative to similar compositions that do not include metal-containing compounds. For example, growth of bacteria or fungi is limited by the compositions of the present invention when disks cut from the composition preferably kill at least about 40% or more of the bacteria or fungi placed on them as evidenced by washing away the original bacteria or fungi, attempting to grow colonies on an agar surface, and observing a reduction in the number of colonies that grow in comparison to the original inoculum and a control that does not include one or more polymer-bound metal-containing compositions of the present invention. More preferably, the compositions of the present invention provide at least about 75% reduction, even more preferably, at least about 90% reduction, and most preferably, at least about 99% reduction, in the amount of at least one species of fungus or bacterium detected on a surface of the composition relative to similar compositions that do not include metal-containing compounds under the same conditions, using the test method described in Example 5 below.

An "effective amount" of one or more of the metal-containing compounds of this invention refers to a concentration of polymer-bound metal-containing compound that is sufficient to limit the presence of a microorganism.

The term "contacting" as used in the methods of this invention includes either physical contact of the compositions of this invention with a virus, a bacterium, or a fungus, or exposure without direct physical contact of a virus, a bacterium, or a fungus to the compositions of this invention. Without intending to limit the scope of this invention, many of the polymer-bound metal-containing compositions of this invention may form diffusible substances in the light, such as singlet oxygen, which mediate an antimicrobial effect on the virus, bacterium, or fungus. Therefore, direct physical contact may not be necessary.

The term "bacteriostatic" refers herein to the property of inhibiting bacterial growth but not necessarily killing the bacteria. The term "bactericidal" refers to killing bacteria. The term "fungistatic" refers herein to the property of inhibiting fungal growth but not necessarily killing the fungus. The term "fungicidal" refers to killing the fungus. Thus, the compositions of this invention can be either bactericidal or bacteriostatic or fungicidal or fungistatic or viricidal. Methods for limiting the presence of a bacterium and fungus include "cidal" (i.e., killing) activity. The term microbicidal is used to encompass the terms bactericidal, fungicidal, and viricidal.

The term "substantially non-leaching" means that less than about 200 nanograms of a metal (as coordinated metal) leaches from a 113 mm$^2$ sample (6 mm diameter disk of any thickness) of polymeric material that has been soaked in 2.0 ml biological medium (for example, Trypticase Soy Broth) for 24 hours at room temperature. Determination of the metal concentration can be performed, for example, using Inductively-coupled Plasma-Mass Spectrometry (ICP-MS) as described in the Examples. A low value of leaching for a given polymer-photosensitizer composition (as determined by testing for leaching of the appropriate metal) is consistent with a polymer-bound metal-containing composition having a low level of unbound metal-containing compound.

DETAILED DESCRIPTION OF THE INVENTION

Figure 1:
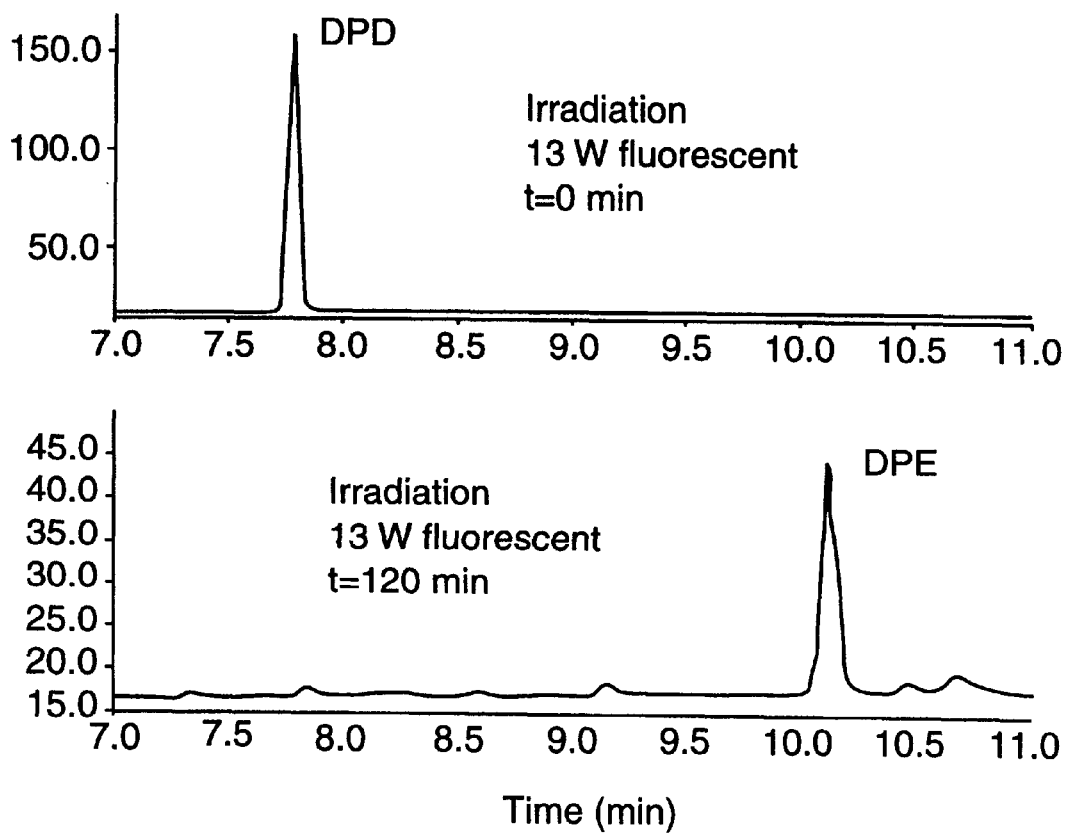
FIG. 1. Gas chromatogram showing conversion of the starting material to the diester indicating singlet oxygen activity. DPD, 2,3-diphenyl-p-dioxene; DPE, ethanediol dibenzoate ester.
Figure 2:
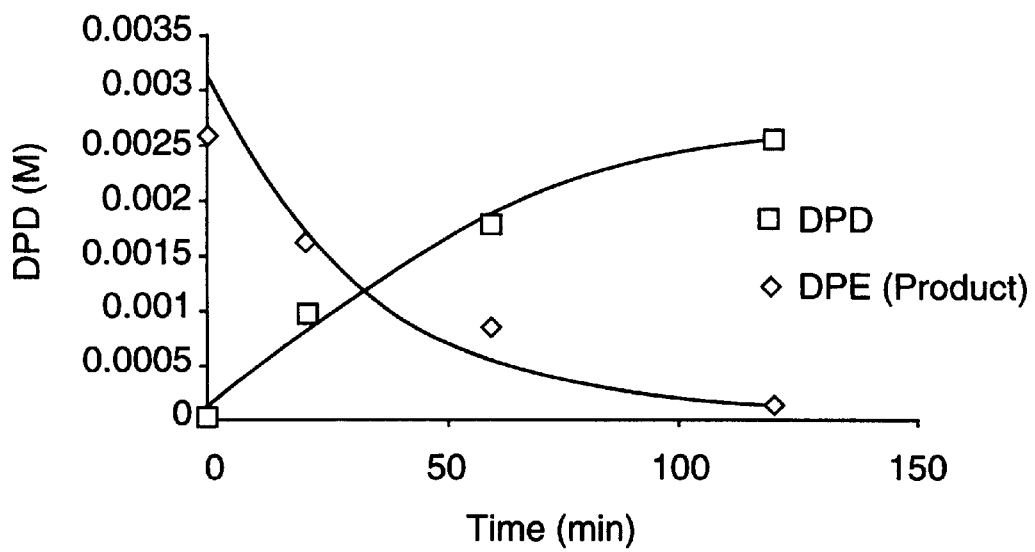
FIG. 2. Singlet Oxygen Production (PVP-TIPS). Conversion of DPD to DPE indicating singlet oxygen activity in PVP-TIPS membrane. DPD(M) indicates molar concentration of DPD.
Figure 3:
FIG. 3. Singlet Oxygen Production (Polypropylene Granules). Conversion of DPD to DPE indicating singlet oxygen activity in poly(propylene) granules. DPD(M) indicates molar concentration of DPD.

The present invention provides polymer-bound metal-containing compositions. The polymer-bound metal-containing compositions of the present invention include a compound of the following formula:

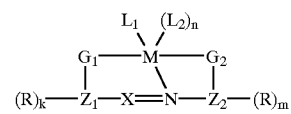

wherein:
$Z_1$ and $Z_2$ each independently represent an arene nucleus, which has from 5 to 14 ring atoms;

$G_1$ and $G_2$ each independently represent a metal ligating group (e.g., oxygen, sulfur, amines, substituted amines, acylamido, sulfonamido), as found in U.S. Pat. Nos. 5,180,705 and 5,314,998, such that $G_1$ and $G_2$ may be contained within or pendant from at least one of $Z_1$ and $Z_2$;

R represents a hydrogen atom, a halogen atom, an alkyl group preferably having less than eight carbon atoms (e.g., a methyl group, ethyl group, hexyl group, etc.), an acylamino group preferably having less than eight carbon atoms (e.g., an acetamido group, benzamido group, hexanamido group, etc.), an alkoxy group preferably having less than eight carbon atoms (e.g., a methoxy group, ethoxy group, benzyloxy group, etc.), a sulfonamido group preferably having less than eight carbon atoms (e.g., a methanesulfonamido group, benzensulfonamido group, etc.), an aryl group preferably having less than eight carbon atoms (e.g., a phenyl group, a 4-chlorophenyl group, etc.), a thiol group, an alkylthio group preferably having less than eight carbon atoms (e.g., a methylthio, a butylthio group, etc.), an arylthio group preferably having less than eight carbon atoms (e.g., a phenylthio group, a 4-methoxyphenylthio group, etc.), an alkylamino group preferably having less than eight carbon atoms (e.g., a cyclohexylamino group, methylamino group, etc.), an arylamino group preferably having less than eight carbon atoms (e.g., an anilino group, a 4-methoxyphenylamino group, etc.), an amino group, an alkoxycarbonyl group preferably having less than eight carbon atoms (e.g., a methoxycarbonyl group, a butoxycarbonyl group, etc.), an acyloxy group preferably having less than eight carbon atoms (e.g., an acetoxy group, a butyryloxy group, a benzoyloxy group, etc.), a nitro group, a cyano group, an alkyl- or aryl-sulfonyl group preferably having less than eight carbon atoms (e.g., a butanesulfonyl group, a benzenesulfonyl group, etc.), an alkyl- or aryl-sulfoxyl group preferably having less than eight carbon atoms (e.g., a butanesulfoxyl group, a benzenesulfoxyl group, etc.), an aryloxyl group preferably having less than eight carbon atoms (e.g., a phenoxy group, etc.), a hydroxyl group, a thioamido group preferably having less than eight carbon atoms (e.g., a butanethioamido group, a benzenethiocarbamoylamido group, etc.), a carbamoyl group preferably having less than eight carbon atoms (e.g., a carbamoyl group, an N-arylcarbamoyl group, an N-alkylcarbamoyl group, etc.), a sulfamoyl group preferably having less than eight carbon atoms (e.g., an N-arylsulfamoyl group, etc.), a formyl group, an acyl group preferably having less than eight carbon atoms (e.g., an acetyl group, a hexanoyl group, a benzoyl group, etc.), a ureido group preferably having less than eight carbon atoms (e.g., an N-ethylureido group, etc.), an aryloxycarbonyl group preferably having less than eight carbon atoms (e.g., a phenoxycarbonyl group, a 4-methoxyphenyloxycarbonyl group, etc.), a silyl group (e.g., a trimethylsilyl group, a phenyldimethylsilyl group, etc.), or a sulfoalkoxy group preferably having less than eight carbon atoms (e.g., a sulfomethoxy group, etc.);

$L_1$ represents a nitrogen heterocycle preferably having a five- or six-membered ring such as a pyridine moiety or an imidazole moiety, wherein the heterocyclic ring is substituted with $R_1$ or $R_2$ or both $R_1$ and $R_2$;

$R_1$ and $R_2$ may each independently represent a hydrogen, a halogen atom (such as an iodine, chlorine, or bromine atom), an alkyl group preferably having less than eight carbon atoms, including vinyl groups, hydroxyalkyl groups, and the like, an acylamino group preferably having less than eight carbon atoms, an alkoxy group preferably having less than eight carbon atoms, a sulfonamido group preferably having less than eight carbon atoms, an aryl group preferably having less than eight carbon atoms, an alkylthio group preferably having less than eight carbon atoms, an aLkylamino group preferably having less than eight carbon atoms, an alkoxycarbonyl group preferably having less than eight carbon atoms, an acyloxy group preferably having less than eight carbon atoms, an alylsulfonyl group preferably having less than eight carbon atoms, an alkylsulfoxyl group preferably having less than eight carbon atoms, an alkylcarbamoyl group preferably having less than eight carbon atoms, an alkylsulfamoyl group preferably having less than eight carbon atoms, a formyl group, an acyl group preferably having less than eight carbon atoms, a silyl group, or a sulfoalkoxy group preferably having less than eight carbon atoms; or a polymer-bound group. At least one of $R_1$ and $R_2$ is a polymer-bound group.

A polymer-bound group may be a polymer that is covalently attached to the heterocyclic ring either through a backbone atom, a side chain atom, or a terminal atom of a polymer chain. Alternatively, the polymer-bound group may be a group that is sterically entangled with a polymer chain, such as might arise by dinerization, oligomerization, or polymerization of a reactive group attached to the heterocyclic ring in the presence of a preformed polymeric matrix. Preferably, the polymer-bound group includes a polymer covalently attached to the heterocyclic ring.

When $R_1$ or $R_2$ represents a polymer-bound group, the polymer may be any suitable type of polymer known in the art such as an addition polymer, a condensation polymer, a random complymer, a block copolymer, and the like, and combinations thereof. Preferred groups include polymer types such as addition polymers and condensation polymers. Examples of addition polymers include, but are not limited to: acrylate (such as that disclosed in U.S. Pat. No. 5,585,407 (Patel)), acrylic, vinyl, polyolefin and olefinic polymers; polyacrylates; polyurethanes; regenerated cellulose, for example, viscose rayon; and cellulose esters, for example, cellulose acetate, as well as copolymers. Examples of condensation polymers include, but are not limited to: polyesters; polycarbonates; polyethers; polyimides; polyureas; and polyamines; as well as copolymers. Certain silicone elastomers such as those formed by hydrosilation and silane condensation reactions, as well as epoxy resins may also be suitable. Preferred polymers include vinyl polymers, vinyl copolymers, and polyurethanes.

$L_2$ represents a monodentate or polydentate (e.g., bidentate) ligand, such as: water; ammonia; halides (e.g., fluorine, chlorine, etc.); thiocyanate; cyanide(–1); azide(–1); carbon monoxide; alkyl and aryl isocyanides (e.g., methylisocyanide, phenylisocyanide, etc.); alkyl and aryl nitriles (e.g., acetonitrile, benzonitrile, etc.); phosphines $P(R_2)_3$, amines $N(R_2)_3$, arsines $As(R_2)_3$, sulfides $S(R_2)_2$ (wherein each $R_2$ independently represents an alkyl or aryl group); heteroarenes (e.g., pyridine, quinoline, etc.); nitrate(–1); and sulfate(–2); alkylene and arylenediamines (e.g., ethylenediamine, 1,2-benzenediamine, tetramethylethylenediamine; etc.); polycyclic arenes with two or more aromatic nitrogen atoms (e.g., bipyridyl; 1,10-phenanthroline; etc.); oxalate(–2); alkyldiketonates (e.g., acetylacetonate(–1), etc.); N,N-dialkyldithiocarbamates(–1); ethylenediamine; 8-hydroxyquinolate(–1); and diarylgyloximates(–2);

X represents nitrogen or a methine group;

M is a platinum or palladium atom; and k, m, and n are whole numbers less than or equal to 4.

Preferred polymer-bound metal-containing compositions include compounds having the following formula:

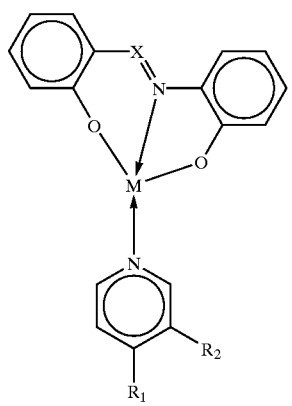

wherein:
R$_1$ and R$_2$ each independently represent H and a polymer-bound group, wherein at least one of R$_1$ and R$_2$ is a polymer-bound group; and
X represents nitrogen or a methine group.

Particularly preferred compounds of the above formula include compounds wherein R$_1$ represents a polymer-bound group including a polymer selected from the group consisting of vinyl polymers, vinyl copolymers, and polyurethanes; R$_2$ represents H, and X represents nitrogen or a methine group.

The preferred metal-containing compounds of the above formula can be prepared by methods that include reacting a prepolymer or polymer with a metal-containing monomer and/or polymerizing or copolymerizing metal-containing monomers of the following formula:

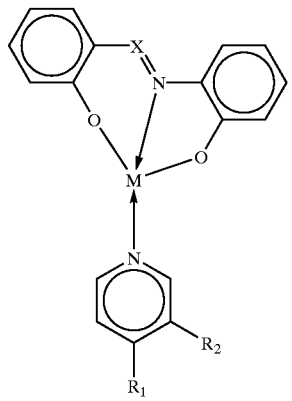

wherein:
R$_1$ and R$_2$ each independently represent H, vinyl, and CH$_2$OH, wherein at least one of R$_1$ and R$_2$ is vinyl or CH$_2$OH; and
X represents nitrogen or a methine group.

Particularly preferred metal-containing monomers of the above formula include where R$_1$ represents vinyl or CH$_2$OH, R$_2$ represents H, and X represents nitrogen or a methine group.

The metal-containing monomers of the present invention can be synthesized from the corresponding O,O'-dihydroxyazo- or O,O'-dihydroxyazomethine compound dianion by displacement of three chlorines in the required tetrachlorometallate and subsequent loss of the remaining chlorine coincident with substitution of a nitrogen heterocycle. Methods for synthesizing the metal-containing azo monomers of this invention are described in U.S. Pat. Nos. 6,248,733 (Landgrebe et al.), 5,166,326 (Smith), 5,461,155 (Smith), 5,180,705 (Smith) and 5,314,998 (Smith). Methods for synthesizing the metal-containing azomethine monomers of this invention are described in U.S. Pat. No. 6,248,733 (Landgrebe et al.).

Compositions including metal-containing monomers may be prepared in a variety of ways. For example, polymers may be prepared by including one or more metal-containing monomers in a polymerization reaction, for example, an addition or condensation polymerization, so as to incorporate the metal-containing compound into the polymer. For example, metal-containing vinyl monomers may be included in free radical polymerization reactions to produce homo- or co-polymers incorporating the metal-containing monomers. As another example, hydroxy functional metal-containing monomers may be reacted with isocyanate functional prepolymers or polymers to produce polyurethanes incorporating the metal-containing monomers.

Such polymers may alternatively be made by reacting an appropriately-substituted metal-containing compound or precursor thereof with a polymer (as occurs in grafting of a metallated dye molecule onto a polymer).

Where the term "group" or "nucleus" is used in describing substituents, substitution is anticipated on the substituent. For example, "alkyl group" includes vinyl groups, ether groups (e.g., CH$_3$—CH$_2$—CH$_2$—O—CH$_2$—), haloalkyls, nitroalkyls, carboxyalkyls, hydroxyalkyls, etc. Similarly, the term "arene nucleus" refers, for example, to not only phenyl, but to chlorophenyl, ethylphenyl, and naphthyl as well.

The concentration of the metal-containing compounds in compositions of the present invention, the light source, intensity or irradiance, spectral properties of the light source, and duration of the illumination can affect the performance of the compositions. Those of ordinary skill in the art will appreciate that the concentration of the metal-containing compounds in compositions of the present invention, light intensity, and the like can be optimized in view of this specification without undue experimentation. Methods are provided in the examples for preferred techniques and formats for optimizing the growth-inhibiting properties of these compositions. Other testing regimes can be readily generated by those skilled in the art, particularly in view of the guidance provided throughout the examples and in view of clinical laboratory testing standards and manuals.

Significantly, the polymer-bound metal-containing compositions of the present invention can be used in methods of limiting the presence of a microorganism. Typically, this involves exposing the composition to light in the presence of the microorganism. Although not intending to be necessarily limiting, it is believed that this results in the formation of singlet oxygen.

U.S. Pat. No. 6,248,733 (Landgrebe et al.) disclosed the use of metal-containing compounds in polymeric compositions (e.g., porous fabrics). Typically, leaching of the metal-containing compound was required to observe antimicrobial activity. For certain embodiments of the compounds described therein, specifically, wherein R$_1$ included a long chain organic group containing, e.g., 8 or 9 carbon atoms, no antimicrobial activity was observed. Compositions of the present invention have low levels of leachable metal. Thus, it is surprising that a polymer-bound metal-containing composition possesses antimicrobial activity. The present invention also obviates concerns about leaching colored photosensitizers from the compositions of the present invention that might result in colorizing materials in which the compositions contact. Thus, the present invention offers benefits in addition to those disclosed in U.S. Pat. No. 6,248,733.

Light exposure can include exposure from a directed light source or from ambient light. Preferably, compositions of this invention are exposed to light of wavelength of at least about 200 nanometers (nm) and less than about 900 nm. More preferably the light has wavelength of at least about 400 nm and less than about 850 nm. Convenient and sufficient light sources are those typically used for fluorescent lighting of laboratories and offices as well as Light Emitting Diode (LED) sources, incandescent sources, sunlight, and lasers. Specific compositions of this invention can optimally be activated with a particular wavelength of light. Without intending to limit the scope of this invention, the spectral output of the light source likely overlaps with the absorption spectrum of the polymer-bound metal-containing compound of the composition as measured in the composition. In one embodiment, the compositions are exposed to an irradiance of at least 270 mW/cm$^2$ for about five minutes, but those of ordinary skill in the art will readily appreciate that brighter light sources allow for reductions in the duration of illumination time.

Light activation can occur with continuous, pulsating, or periodic exposure to light. Those with ordinary skill in the art will recognize that optimal activation will depend on the intensity and the duration of light, but that a range of intensities and durations of light exposure can be used to activate the light-responsive compositions of this invention.

In one embodiment, the microorganism is a virus, for example, an enveloped virus such as HIV, a member of the Herpesvirus group, or an influenza virus. In another embodiment, the microorganism is a bacterium such as a Gram-positive bacterium or a Gram-negative bacterium. In another embodiment, the microorganism is an antibiotic-resistant Gram-positive bacterium or an antibiotic-resistant Gram-negative bacterium. In yet another embodiment, the microorganism is a fungus, such as a yeast.

Both DNA and RNA viruses (including RNA retroviruses) are inactivated, and Gram-negative bacteria, Gram-positive bacteria, and fungi are limited in growth, using the compositions of the present invention in combination with light.

There are a variety of viruses that can be inactivated using the methods of this invention. These viruses include viruses with single or double-stranded nucleic acid genomes, DNA or RNA viruses and including enveloped as well as some non-enveloped viruses. Preferred viruses that are inactivated using the compositions of the present invention are enveloped viruses. The examples (below) provide specific exemplary methods for determining whether a particular type of virus, fungus, or bacterium is inhibited by the compositions of this invention with exposure to light. Those of ordinary skill in the art of microbiology will be able to determine whether a particular compound of this invention limits the presence of a virus, a bacterium, or a fungus according to this invention and in view of the art of microbiology without undue experimentation.

Viruses having negative single-stranded RNA genomes include Orthomyxoviridae, Rhabdoviridae, Paramyxoviridae, Bunyaviridae, and Filoviridae. These are enveloped viruses. Orthomyxoviridae include the influenza viruses A, B, and C. Rhabdoviridae include rabies virus and vesicular stomatitis virus. Paramyxoviridae include parainfluenza virus of mammals (including mumps virus) and pneumovirus (such as respiratory syncytial viruses of man and cattle). Bunyaviridae include hantavirus, which causes Korean hemorrhagic fever and hantavirus pulmonary syndrome. Filoviridae include Marburg virus and Ebola virus.

Viruses having positive single-stranded RNA genomes include Picornaviridae (non-enveloped), Retroviridae, and Togaviridae. Picornaviridae include polioviruses, coxsackieviruses, hepatitis A virus, and rhinovirus. Retroviridae include, for example, human immunodeficiency virus (HIV), simian immunodeficiency virus (SIV), and equine infectious anemia virus (EIAV). Togaviridae include Semliki Forest virus, yellow fever virus, Dengue virus, tick-borne virus, and rubella virus. Parvovirus (non-enveloped) is the only virus having a single-stranded negative-sense DNA genome. This virus primarily infects cats and dogs.

All other DNA viruses are double-stranded. Double stranded viruses include Papovaviridae, Adenoviridae, Herpesviridae, Poxviridae, and Hepadnaviridae. With the exception Herpesviridae, these viruses are non-enveloped viruses. Papovaviridae include papillomaviruses causing warts and tumors. Adenoviridae include Mastadenovirus and a variety of viruses capable of infecting the respiratory tract. Herpesviridae include herpes simplex 1 and 2, varicella zoster virus, cytomegalovirus, Epstein-Barr virus, human herpesvirus 6, antibodies to which are now known to be responsible for multiple sclerosis, and human herpesvirus 7. Poxviridae include variola and other pox-producing viruses. Hepadnaviridae include human hepatitis B virus.

A variety of bacteria are growth inhibited by the polymer-bound metal-containing compositions of this invention in combination with light. These include, but are not limited to, *Enterococcus faecium, Staphylococcus aureus, Escherichia coli, Pseudomonas aeruginosa*. Other bacteria that can be tested for growth inhibition in the presence of the compositions of this invention, include, but are not limited to, other species of Streptococcus, Corynebacterium, Listeria, Neisseria, and Enterobacteriaceae (which includes the genera Escherichia, Salmonella, Shigella). The coliforms are Gram-negative rods, generally in the family Enterobacteriaceae. These bacteria are associated with disease.

While microorganisms present in a composition of the present invention in combination with light will be limited in growth, the microorganisms are not required to be contained within the composition to be limited in growth. Microorganisms in liquids contacting a surface coated with compositions of the present invention will likewise be limited in growth Also, microorganisms present in solids that come in contact with or in proximity to compositions of the present invention may be growth limited due to diffusion of singlet oxygen to the other surfaces.

Several pathogenic species of fungi exist, including *Candida albicans*, which causes yeast infection of the oral cavity known as thrush and an infection of the female reproductive tract known as vulvovaginitis. *Candida albicans* is becoming increasingly common as an agent causing infection and pathogenic sequelae. Those of ordinary skill in the art of microbiology will appreciate that various fungi can be tested for their sensitivity to compositions of this invention.

The polymer-bound metal-containing compositions of the present invention may further include other materials as required to provide the desired physical and functional properties. For example, the compositions of the present invention may include polymers, not only as polymer-bound metal-containing compounds, but also as unbound polymers present in the composition. Such polymers can be purchased from a chemical supplier or prepared according to methods known to those skilled in the art of polymer synthesis. A variety of polymers can be used in the invention. Polymers are preferably chosen to resist attack by singlet oxygen.

Examples of suitable polymers include, but are not limited to, addition polymers, for example, acrylate (such as that disclosed in U.S. Pat. No. 5,585,407 (Patel)), acrylic, vinyl, polyolefin and olefinic polymers; polyacrylates; polyurethanes; regenerated cellulose, for example, viscose rayon; cellulose esters, for example, cellulose acetate; condensation polymers such as polyesters; polycarbonates; polyethers; polyimides; polyureas; and polyamines; as well as copolymers. Certain silicone elastomers such as those formed by hydrosilation and silane condensation reactions, as well as epoxy resins may also be suitable. Suitable polymers may be obtained in a water- or solvent-soluble solid form, or as a dispersion or emulsion in water or solvent. Examples of commercially available polymers include STANCE floor finish (3M Company, St. Paul, Minn.), VITEL polyester (Goodyear Chemicals, Akron, Ohio), and polycarbonate resin (Aldrich Chemical, Milwaukee, Wis.). Preferably, for certain embodiments, the polymers are coatable, but this is not a necessary requirement. For other embodiments, the polymers are extrudable. In certain particularly preferred embodiments, non-cellulosic polymers are preferred, and non-addition polymers are even more preferred, due to the carbon-carbon double bonds with allylic hydrogens that are present in many olefinic addition polymers and the undesirable polymer degradation that may occur as a result of reaction with singlet oxygen.

Polymers included in compositions of the present invention may be hardened. A hardened composition can be achieved by soldifying a liquid polymer, evaporating solvent from a polymer solution or dispersion, crosslinking or otherwise curing a polymer to render it insoluble, by extruding or molding a polymer, etc. A hardened polymer does not necessarily mean that the polymer is hard and inflexible; rather it means that the polymer is cured or otherwise rendered solid. In fact, in certain applications such as coatings on flexible or de-formable substrates a flexible "hardened" polymer composition may be preferred. Furthermore, depending on the type of polymer, a "hardened" polymer may have been cooled and solidified (as for a thermoplastic) or cured (i.e., polymerized and/or crosslinked) from polymer precursors.

The polymer-bound metal-containing composition of the present invention may, for example, be in the form of a fiber, free-standing film, or coating. It may be a cast, molded, or extruded article. The compositions of the present invention can take the form of textile articles, for example, cleaning cloths, wipes, surgeon's gowns, medical instruments, bed linen, wound dressings, and bandages. They may alternatively take the form of self-supporting films, for example, for use in food packaging or wound dressings. Wound dressings may be sterilized by exposure to light before application and then covered up, once they have been placed over a wound, to restrict or eliminate exposure to light in order to stop the formation of singlet oxygen, which may be harmfull and consequently undesirable in a wound environment.

The compositions and articles of the invention are useful in medical and clinical auxiliaries for domestic and hospital use, for example, for tubing, bags, and mats used in dialysis procedures, for example, for kidney dialysis. The articles may take the form of polymer laminates with an antimicrobial surface for use in hygienic applications, in which one or more layers of the laminate contains or consists of a polymer-bound metal-containing composition. Preferably, at least one surface of the laminate contains or consists of a polymer-bound metal-containing composition.

Compositions of the present invention can be incorporated into cloth for use as antimicrobial wipes. Similarly, the compositions can be used for surface sterilization, for example, in home, day-care, industrial, and hospital settings, for cleansing toys, equipment, medical devices and work surfaces. A variety of equipment, disposables and devices such as sutures and bandages, hypodermic needles and containers can be sterilized using the compositions, according to this invention.

The metal-containing compounds of the present invention are extremely light and heat stable. Solutions of the metal-containing compounds can be prepared in DMSO at an optical absorption of approximately 1.0 at the wavelength of maximal absorption of the metal-containing compound between 400 nm to about 700 nm. Solutions prepared in this way do not show substantial changes in absorption spectrum (including optical density) after one year of being stored in room light. The metal-containing compounds are also stable at temperatures up to at least about 300° C.

The following examples demonstrate the preparation of the polymer-bound metal-containing compositions. The examples also demonstrate the performance, or the means of testing the performance, of the compositions in generating singlet oxygen, in inactivating viruses, in inhibiting viral replication, and in limiting the growth or presence of bacteria and fungi. All references and publications are incorporated by reference into this disclosure.

The present invention is illustrated by the following examples. It is to be understood that the particular examples, materials, amounts, and procedures are to be interpreted broadly in accordance with the scope and spirit of the invention as set forth herein.

EXAMPLES

Example 1

Synthesis of the Metal-Containing Monomers

Reagents for chemical synthesis were obtained from Aldrich (Milwaukee, Wis.) unless otherwise noted. Platinum and palladium azo dye monomers may be synthesized according to the known literature procedures. Specifically, Monomer 1A ($R_1$=vinyl, $R_2$=H, X=N, M=Pt) was synthesized as disclosed in U.S. Pat. No. 5,180,705 (Smith). Monomer 1B ($R_1$=$CH_2OH$, $R_2$=H, X=N, M=Pt) was synthesized as taught in U.S. Pat. No. 5,180,705 (Smith) following the procedure used in Example 3, except that 4-hydroxymethylpyridine was used instead of vinylpyridine. Platinum and palladium azomethine dyes may be synthesized according to the procedures described below for Monomer 1C and Monomer 1D. Room temperature is at ambient temperature, generally from about 20° C. to about 25° C.

Synthesis of Monomer 1C ($R_1$=vinyl, $R_2$=H, X=CH, M=Pt)

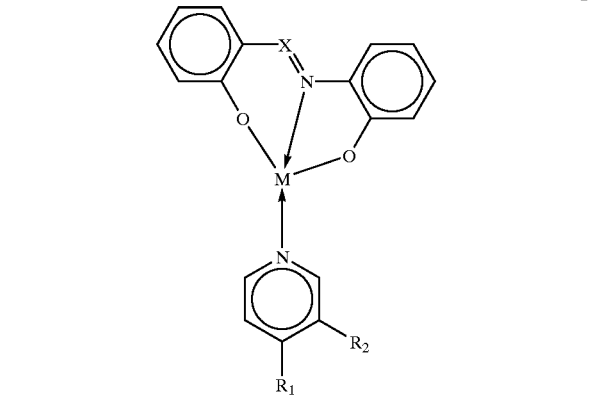

A solution of 2-salicylideneaminophenol (0.320 grams (g), 1.5 millimoles (mmol), TCI-America, Portland, Oreg.) in dimethyl sulfoxide (15 milliliters (ml)) at 100° C. was added to a solution of potassium tetrachloroplatinate (0.685 g, 1.65 mmol) in dimethyl sulfoxide (15 ml) at 100° C. Next, potassium carbonate (0.600 g) was added and the resulting mixture heated at 150° C. for 10 minutes (min). The reaction mixture was allowed to cool to 100° C. and then 4-vinylpyridine (0.600 ml) was added. The reaction mixture was stirred at room temperature for 18 hours (h). The reaction mixture was poured into water (50 ml) and then extracted once with diethyl ether (150 ml) and once with chloroform (150 ml). The diethyl ether and chloroform extracts were combined. The combined extracts were washed sequentially with 3N hydrochloric acid (twice 50 ml), water (twice 100 ml), and brine (100 ml). The organic solution was dried over anhydrous magnesium sulfate, filtered and concentrated to give an orange solid. The solid was dissolved in a minimum amount of chloroform and passed through a column of silica gel (20×5 centimeters (cm)) while eluting the column with chloroform (250 ml). The eluent was concentrated to give an orange solid. The solid was recrystallized from ethanol to give 0.068 grams of IC as an orange solid; $^1$H NMR (500 MHz; CDCl$_3$): δ 5.70 (d, 1H, J=10.8 Hz); 6.14 (d, 1H, J=17.6 Hz); 6.70–6.82 (m, 3H); 7.10–7.17 (m, 2H); 7.26–7.28 (m, 1H); 7.46–7.51 (m, 3H); 7.66 (dd, 1H, J$_1$=7.9 Hz, J$_2$=1.6 Hz); 7.81 (d, 1H, J=8.3 Hz); 8.65 (s, 1H); 9.16 (dd, 1H, J$_1$=5.4 Hz, J$_2$=1.6 Hz); $^{13}$C{$^1$H} NMR (125 MHz; CDCl$_3$): δ 114.21, 115.23, 116.08, 117.77, 121.14, 121.56, 121.67, 128.16, 132.34, 133.04, 133.25, 140.00, 142.77, 146.45, 149.26, 161.75, 167.01.

Synthesis of Monomer 1D (R$_1$=CH$_2$OH, R$_2$=H, X=CH, M=Pt)

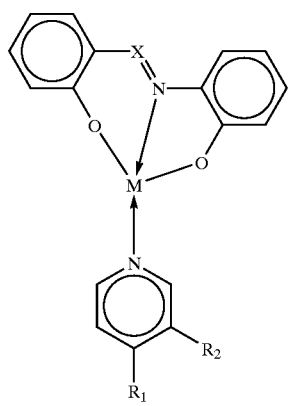

A solution of 2-salicylideneaminophenol (0.320 g, 1.5 mmol, TCI-America, Portland, Oreg.) in dimethyl sulfoxide (15 ml) at 100° C. was added to a solution of potassium tetrachloroplatinate (0.685 g, 1.65 mmol) in dimethylsulfoxide (15 ml) at 100° C. Next, potassium carbonate (0.600 g) was added and the resulting mixture heated at 150° C. for 10 min. The reaction mixture was allowed to cool 10 to 100° C. and then 4-pyridinecarbinol (0.607 g) was added. The reaction mixture was stirred at room temperature for 18 h.

The reaction mixture was poured into water (50 ml) and then extracted once with diethyl ether (150 ml) and once with chloroform (150 ml). The diethyl ether and chloroform extracts were combined. The combined extracts were washed sequentially with 3N hydrochloric acid (twice 50 ml), water (twice 100 ml), and once with a saturated aqueous solution of NaCl. The organic solution was dried over anhydrous magnesium sulfate, filtered and concentrated to give an orange solid. The solid was recrystallized from ethanol to give 0.080 grams of 1D as dark brown crystals; $^1$H NMR (500 MHz; d$_6$-DMSO): δ 4.70 (d, 2H, J=5.6 Hz); 5.67 (t, 1H, J=5.6 Hz); 6.67 (dt, 1H, J1=7.3 Hz, J2=1.6 Hz); 6.78 (t, 1H, J=7.3 Hz); 7.00–7.08 (m, 2H); 7.21 (d, 1H, J=8.3 Hz); 7.47 (dt, 1H, J1=7.7 Hz, J2=1.7 Hz); 7.66 (d, 2H, J=6.6 Hz); 7.88 (dd, 1H, J1=8.1 Hz, J2=1.7 Hz); 8.09 (d, 1H, J=8.4 Hz).

Example 2

Preparation of Polymer-Bound Metal-Containing Compositions

Reagents for preparation of the compositions were obtained from Aldrich (Milwaukee, Wis.) unless otherwise noted.

Sample A: A Polyurethane-Bound Metal-Containing Composition Prepared using 1% Monomer 1B A flask was charged with trimethylol propane (0.5 g), dimethylolpropionic acid (4.0 g, Trimet Technical Products, Mallinckrodt, Inc., Allentown, Pa.), Tego diol HSi2311 (27.0 g, Goldschmidt Chemical Corporation), FMDA11 polydimethylsiloxane, MW1000 (22.0 g, Chisso Corporation, Silicon Chemicals Division, Tokyo, Japan), Terathane 2000 polytetramethylene ether oxide diol, MW2000 (14.46 g, Dupont, Wilmington, Del.), N-methylpyrolidone (15 g, BASF), Tinuvin 292 UV stabilizer (0.50 g, Ciba Geigy, USA), and Tinuvin 284 UV stabilizer (1.0 g, Ciba Geigy, USA), then Desmodur-W isocyante (32.5 g, Bayer Corp., USA). The components were stirred for 2 minutes after which 0.04 grams of T-12 (dibutyltindilaurate, Air Products) was added. The mixture was stirred for 8 hours under inert atmosphere at 80° C. Before completion of the reaction, 1 gram of Monomer 1B (R$_1$=CH$_2$OH, R$_2$=H, X=N, M=Pt) was added to the prepolymer. The reaction was determined to be complete when titration of isocyanate (standard dibutylamine-dilute HCl titration) showed all isocyanate to have reacted. A 100 gram portion of the mixture was then dispersed in water (280 g) under high shear and to the dispersion was added triethylamine (2.61 g), ethylenediamine (0.5 g) and a solution of DICYKAN (4,4 diaminodicyclohexyl-methane; BASF, USA, 7 grams in 12 grams of N-methylpyrrolidone). The components were allowed to mix at high sheer for 4 minutes. The dispersion was transferred to a high pressure homogenizer (4000 psi) and allowed to homogenize for 10 minutes after which it was mixed again for 3 hours at 500 rpm. Polyurethane films were cast onto polyester release liners and allowed to cure for 7 days at 20° C. after which they were tested for dye leaching, microbicidal activity, and singlet oxygen generation as described below.

Sample B: A Polyurethane-Bound Metal-Containing Composition Prepared Using 0.5% Monomer 1B Sample B was prepared in a manner similar to that of Sample A, except 0.5% of Monomer 1B was used.

Sample C: A Pore-filled TIPS Membrane Including a Polymer-Bound Metal-Containing Composition Prepared using Monomer 1A TIPS membrane (Thermally Induced Phase Separation) membrane of polypropylene, can be prepared according to U.S. Pat. No. 4,539,256 (Shipman). A TIPS membrane including Monomer 1A (R$_1$=vinyl, R$_2$=H, X=N, M=Pt) was prepared by mixing 4-vinylpyridine (1 g), divinylbenzene (50 mg), dye 1A (14 mg) and Irgacure 651 photoinitiator (46 mg, Ciba Specialty Chemicals, USA). The solution was absorbed onto a 13 cm×13 cm piece of polypropylene TIPS membrane and then placed between two release liners. Excess monomer solution was squeezed out and the film was irradiated with a UV lamp for 10 minutes on each side, washed twice with methanol, and then dried in vaccuo for 5 minutes. The resulting TIPS membrane was tested for dye leaching, microbicidal activity, and singlet oxygen generation as described below.

Sample D: A Polpropylene-Bound Metal-ContaininE Composition Prepared Using 0.25% Monomer 1A Unstabilized polypropylene (130 g, Quantum 8310 containing 3% polyethylene, Equistar Petrochemicals Limited, Houston, Tex.) was mixed with 0.33 g of Monomer 1A ($R_1$=vinyl, $R_2$=H, X=N, M=Pt) and 0.25 ml Lupersol initiator (Elf Atochem North America, Inc., Philadelphia, Pa.) and then transferred to the mixing chamber of a Hakke melt mixer at 170° C. The temperature of the mixing chamber was held at 170° C. for 15 min, then cooled to 150° C. for five min. The resulting polymer was cast into a film (except where noted below) and was characterized and tested for dye leaching, microbicidal activity, and singlet oxygen generation as described below.

Sample E: A Polyproivlene-Bound Metal-Containing Composition Prepared Using 1% Monomer 1A Sample E was prepared in a manner similar to that of Sample D, except 1% of Monomer 1B was used.

Example 3

Testing of Dye Leaching from Polymer-Bound Metal-Containing Compositions

Leaching of metal from the compositions was determined using ICP-MS. A 6 mm disk sample of the composition (113 mm²) was soaked in 2.0 ml Trypticase Soy broth (BDL via VWR, catalog #4311771) for 24 h at room temperature. Then 0.5 g of the sample was accurately weighed into a 15 ml metal-free centrifuge tube. Each sample was analyzed in duplicate. A solution (1 ml) of 40% HCl/10% HN03 and 10 ml of 10 ppm Bismuth internal standard were added to each sample. Deionized water was added to make 10 ml of solution.

Samples were analyzed on a Perkin-Elmer ELAN 6000 ICP-MS. The results are reported in parts per billion, which is equivalent to nanograms metal element per gram of sample tested. (For the 2 ml (approximately 2 g) samples tested, 200 nanograms metal/gram sample is equivalent to 100 ppb leaching, the level below which the samples are considered to be substantially non-leaching.)

Results of Dye Leaching Tests

| Sample | Leaching (parts per billion metal) |
|---|---|
| Sample D: 0.25 weight % Monomer 1A bound to polypropylene | <1.5 ppb |
| Sample C: TIPS memebrane with bound Monomer 1A | <1.5 ppb |
| Sample B: 0.5 weight % Monomer 1B bound to polyurethane | 21 ppb |
| Sample A: 1.0 weight % Monomer 1B bound to polyurethane | 65 ppb |

The results are consistent with a polymer-bound metal-containing composition.

Example 4

Testing of Microbicidal Activity of Polymer-Bound Metal-Containing Compositions

Testing of Compositions for Viricidal Activity Against Equine Infectious Anemia Virus (EIAV)

The aforementioned compositions are tested for viricidal activity against EIAV by determining loss of infectivity for equine dermal (ED) cells (ATCC CCL57). The procedure used is as follows:

Day 1. ED cells are seeded into 6-well tissue culture plates (Corning Co., #25810) at $5 \times 10^5$ cells per well in Dulbecco's Modified Eagle's Medium (#D5648) with 20% fetal calf serum (GibcoBRL Co., #26140-038). The cells are incubated (under $CO_2$) until "Day 2" at 37° C.

Day 2. Virus is treated with the composition (6 mm disk) by placing virus-laden Hanks buffer solution onto a surface treated with the composition or an article having the composition on its surface. (Unless otherwise noted, all experimental manipulations are done in ambient light.)

1. Preparation of "test solution"

Hanks balanced buffer solution (1.0 ml, having $10^4$ infectious units of virus) without calcium chloride or magnesium sulfate (HBSS, Sigma Chemical Co., #H2387) with 2% fetal calf serum is placed into contact with the composition. Samples are placed into individual wells of duplicate 24-well tissue culture plates (Corning, #25820). One plate is wrapped in aluminum foil and served as the dark control for those experiments for which a control sample is run. The other plate is placed on a benchtop and exposed to fluorescent room light for 30 minutes (except where noted below) at room temperature (irradiance=272 $\mu W/cm^2$).

2. ED cells in 6-well plates are inoculated with polybrene (Sigma Chemical Co., #P4515) to a final concentration of 8 mg/ml and test solution (from step 1) containing the polymer-bound metal-containing composition (6 mm disk). Cells are incubated 5 days at 37° C. in the dark.

Day 7. Immunohistochemical Detection of Virus-Infected Cells.

1. Medium is aspirated and cells are rinsed once with 3 ml TNF (10 mM Tris (pH 7.5), 150 mM NaCl, 1% fetal bovine serum) and fixed with 100% methanol for 5 min. Cells are rinsed twice with 3 ml TNF and incubated 30 min. with 0.5 ml horse anti-EIAV serum (convalescent sera at 1:800 dilution in HBSS) with rocking.

2. Cells are rinsed three times with 3 ml TNF and incubated for 30 min. with 0.5 ml anti-horse HRP antibody (Cappel/Organon Teknika Corp., Lot #35426) with rocking.

3. Cells are rinsed three times with 3 ml TN (no FBS) and incubated with 2 ml AEC substrate (Sigma Chemical Co., #A6926) in 0.05 M sodium acetate 1N,N-dimethyl formamide (Sigma Chemical Co., #D8654) buffer for 20 min. in the dark. Cells are rinsed with distilled water and allowed to dry.

4. Positive foci of infected cells are counted with light microscopy and the number of focus forming units (FFU) per ml of inoculum is calculated. The FFU of samples treated with the potential viricidal composition and light are compared to those for samples kept in the dark.

One skilled in the art of microbiology will recognize that this protocol could be used for evaluating the viricidal activity of the compositions described herein.

Testing of Polymer-Bound Metal-Containing Compositions for Viricidal Activity Against Human Immunodeficiency Virus 1 (HIV-1) and Herpes Simplex Virus-1 (MSV-1)

These tests can be performed by Southern Research Institute, Birmingham, Ala., according to the following procedures.

Human Immunodeficiency Virus Type-1 (HIV-1) Testing

Concentrated HIV/RF (0.1 ml) is placed onto a disk of the composition situated in a well of a 24-well plate. The plate is allowed to sit under regular fluorescent lighting on the lab benchtop for 30 min. A dark control is run for each concentration tested. Next, serial dilutions are made from the well samples and are used to inoculate MT2 cells at $10^4$ cells/well. Plates are allowed to incubate at 37° C., 5% $CO_2$ for seven days. The results are reported as Log Reduction in Virus Titer.

Herpes Simplex Virus Type 1 (HSV-1) Testing

The protocol for HSV-1 testing is essentially identical to that for HIV-1 testing, except that Vero cells are inoculated with polymer-bound metal-containing composition-treated HSV-1 particles.

Example 5

Testing of Polymer-Bound Metal-Containing Compositions for Limiting Growth of Bacteria and Fungi Testing of Sample A (a Polyurethane-Bound Metal-Containing Composition Prepared using 1% by Weight of Monomer 1B) for Ability to Limit Growth of *Enterococcus faecium*

*Enterococcus faecium* stock was plated onto TSB agar and grown up at 37° C. overnight, at which time several colonies were transferred to PBS (buffer) to give a solution with final concentration of $10^8$ bacteria/ml. Ten microliters of that solution were added to 9990 microliters of PBS to give 10 ml of a solution that contained $10^5$ bacteria/ml. Finally, 100 microliters of that solution were added to 2 ml trypticase soy broth to give about 2 ml of the test solution of bacteria with a concentration of 5000 bacteria/ml.

Into vials containing 2 ml of these bacteria-laden broths were placed six 6 mm disks of Sample A. The vials were placed in a 37° C. incubator 6 inches above two Phillips 15W daylight bulbs (irradiance=1.35 mW/$cm^2$) with light on for 18 hours. No dark control was run for this experiment.

Result:

The broths were clear, indicating that the colonies of *E. faecium* were not allowed to increase in number.

Testing of Sample E (a Polpropylene-Bound Metal-Containing Composition Prepared Using 1% by Weight of Monomer 1A)

*Enterococcus faecium* stock was plated onto TSB agar and grown up at 37° C. overnight, at which time several colonies were transferred to PBS (buffer) to give a solution with final concentration of $10^8$ bacteria/ml. This solution was used to swab two other TSB agar plates to make a potential bacterial lawn on each plate and onto these potential lawns were placed a 6 mm disk of Sample C. One of the plates was wrapped in aluminum foil and placed in a 37° C. incubator overnight. The other was irradiated overnight with visible light (irradiance=40 mW/$cm^2$) at room temperature, and then subsequently placed in the dark in a 37° C. incubator overnight.

Result:

Whereas the dark control showed no zone of inhibition, the sample irradiated with visible light showed a 1-mm zone, indicative of limiting of growth of the bacterium by the polymer-bound metal-containing composition in combination with light.

It will be appreciated by those skilled in the art that the same test methods employed for testing the ability of the compositions of the present invention to limit the growth of bacteria can be used for testing the limitation of growth of fungi.

Example 6

Testing of Polymer-Bound Metal-Containing Compositions for Generation of Singlet Oxygen Singlet oxygen production was measured indirectly by chromatographic detection of the dibenzoate ester of ethanediol (DPE), which forms by reaction of singlet oxygen with 2,3-dipheny-p-dioxene (DPD).

A methanol cast of 2,3-diphenyl-p-dioxene on Sample B was irradiated with a 13 W fluorescent lamp at a distance of 2 cm. After 2.5 hrs the polyurethane was rinsed with methanol, which was analyzed by gas chromatography. The conversion of the starting material to the diester indicating singlet oxygen activity is shown in FIG. 1.

Example 7

Testing of Sample C (TIPS Membrane including Polypropylene-Bound Metal-Containing Composition) for Generation of Singlet Oxygen A (1 cm×1 cm) piece of Sample C was placed in a $10^{-3}$ M solution of DPD (2 mL) and irradiated (13 W fluorent lamp) for 2 hours. Conversion of DPD to diester is shown in FIG. 2.

A similar procedure was used for testing a granular form (100 mg) of Sample D that had not been cast as a film (containing 0.25% dye 1A) where [DPD]=10 4 M. The solution containing the resin was irradiated using eight 8W cool fluoresent lights at a distance of 7.2 cm. Conversion of the DPD is shown in FIG. 3.

It will be appreciated by those skilled in the art that the method of the present invention will make it possible to inhibit microorganism growth in virus-laden, bacteria-laden, or fungi-laden articles or surfaces. Other viruses, bacteria, and fungi can be similarly tested using the methods of this invention without undue experimentation.

The complete disclosures of all patents, patent applications, and publications that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for limiting the presence of a microorganism, the method comprising contacting the microorganism with a polymer-bound metal-containing composition comprising a compound having the following formula:

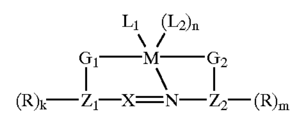

wherein:

$Z_1$ and $Z_2$ each independently represent an arene nucleus, which has from 5 to 14 ring atoms;

$G_1$ and $G_2$ each independently represent a metal ligating group such that $G_1$ and $G_2$ may be contained within or pendant from at least one of $Z_1$ and $Z_2$;

R represents a hydrogen atom, a halogen atom, an alkyl group, an acylamino group, an alkoxy group, a sulfonamido group, an aryl group, a thiol group, an alkylthio group, an arylthio group, an alkylamino group, an arylamino group, an amino group, an alkoxycarbonyl group, an acyloxy group, a nitro group, a cyano group, an alkyl- or aryl sulfonyl group, an alkyl- or aryl sulfoxyl group, an aryloxyl group, a hydroxyl group, a thioarrido, a carbamoyl group, a sulfamoyl group, a formyl group, an acyl group, a ureido group, an aryloxycarbonyl group, a silyl group, or a sulfoalkoxy group;

$L_1$ represents a nitrogen heterocycle substituted with $R_1$ or $R_2$ or both $R_1$ and $R_2$;

$R_1$ and $R_2$ each independently represent a polymer-bound group, a hydrogen, a halogen atom, an alkyl group, a vinyl group, a hydroxyalkyl group, an acylamino group, an alkoxy group, a sulfonamido group, an aryl group, an alkylthio group, an alkylamino group, an alkoxycarbonyl group, an acyloxy group, an alylsulfonyl group, an alkylsulfoxyl group, an alkylcarbamoyl group, an alkylsulfamoyl group, a formyl group, an acyl group, a silyl group, or a sulfoalkoxy group; wherein at least one of $R_1$ and $R_2$ represents a polymer-bound group;

$L_2$ represents a monodentate or polydentate ligand;

X represents nitrogen or a retained group;

M represents a platinum or palladium atom; and k, m, and n are whole numbers less than or equal to 4.

2. The method of claim 1 wherein the method further comprises exposing the composition to an amount of light sufficient to activate the composition.

3. The method of claim 1 wherein the polymer-bound metal-containing composition comprises a compound of the following formula:

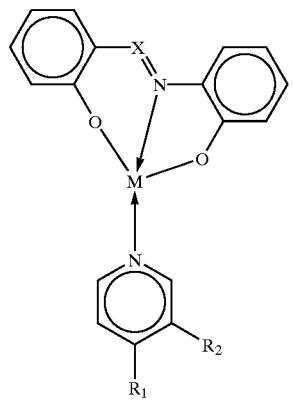

wherein:
$R_1$ and $R_2$ each independently represent H or a polymer-bound group, wherein at least one of $R_1$ and $R_2$ represents a polymer-bound group; and X represents nitrogen or a methine group.

4. The method of claim 3 wherein $R_1$ represents a polymer-bound group comprising a polymer selected from the group consisting of vinyl polymers, vinyl copolymers, and polyurethanes; $R_2$ represents H, and X represents nitrogen or a methine group.

5. The method of claim 1 wherein the microorganism is a virus.

6. The method of claim 5 wherein the virus is an enveloped virus.

7. The method of claim 5 wherein the virus is HIV.

8. The method of claim 5 wherein the virus is a member of the Herpes virus group.

9. The method of claim 5 wherein the virus is an Influenza virus.

10. The method of claim 1 wherein the microorganism is a bacterium.

11. The method of claim 10 wherein the bacterium is a grain-positive bacterium.

12. The method of claim 11 wherein the bacterium is an antibiotic-resistant gram-positive bacterium.

13. The method of claim 10 wherein the bacterium is a gram-negative bacterium.

14. The method of claim 13 wherein the bacterium is an antibiotic-resistant gram-negative bacterium.

15. The method of claim 1 wherein the microorganism is a fungus.

16. The method of claim 15 wherein the fungus is a yeast.

17. The method of claim 1 wherein replication of the microorganism is inhibited by contacting the microorganism with the polymer-bound metal-containing composition.

18. The method of claim 1 wherein the microorganism is killed by the contacting the microorganism with the polymer-bound metal-containing composition.

19. The method of claim 1 wherein the microorganism is present in a liquid that is contacted with the polymer-bound metal-containing composition.

20. The method of claim 1 wherein the microorganism is present in a solid that is contacted with the polymer-bound metal-containing composition.

21. The method of claim 1 wherein the composition further comprises at least one other antimicrobial compound.

22. The method of claim 1 wherein n is a whole number less than or equal to 2.

23. A polymer-bound metal-containing compound of the following formula:

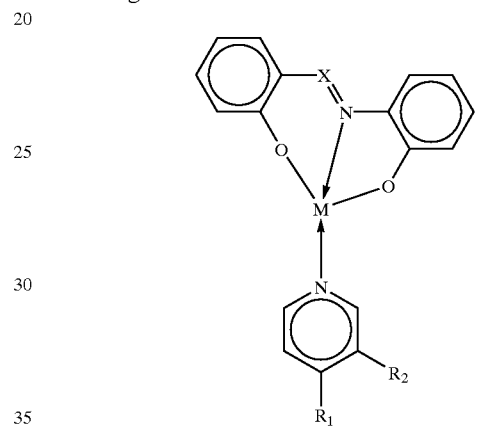

wherein:
$R_1$ and $R_2$ each independently represent H or a polyurethane-bound group, wherein at least one of $R_1$ and $R_2$ represents a polyurethane-bound group;

X represents nitrogen or a methine group; and

M represents a platinum or palladium atom.

24. The compound of claim 23, wherein $R_1$ represents a polyurethane-bound group, $R_2$ represents H, and X represents nitrogen or a methine group.

25. A method of preparing a polymer-bound metal-containing compound of the following formula:

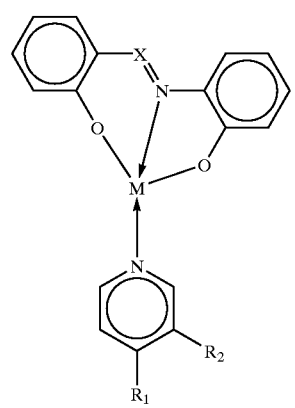

wherein:
$R_1$ and $R_2$ for the polymer-bound metal-containing compound each independently represent H or a polymer-bound group, wherein at least one of $R_1$ and $R_2$ for the polymer-bound metal-containing compound represents a polymer-bound group;

X represents nitrogen or a methine group; and

M represents a platinum or palladium atom;

the method comprising reacting a prepolymer or polymer with a metal-containing monomer of the following formula:

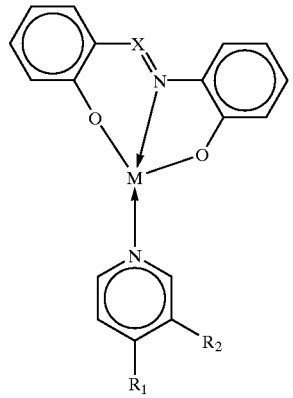

wherein:

$R_1$ and $R_2$ for the monomer each independently represent H or $CH_2OH$, wherein at least one of $R_1$ and $R_2$ for the monomer represents $CH_2OH$;

X represents nitrogen or a methine group; and

M represents a platinum or palladium atom.

26. The method of claim 25, wherein $R_1$ for the monomer represents $CH_2OH$, $R_2$ for the monomer represents H, and X represents nitrogen or a methine group.

27. The method of claim 25, wherein the method comprises reacting an isocyanate functional prepolymer or polymer with the monomer.

28. The method of claim 3 wherein $R_1$ represents a thermoplastic polymer-bound group; $R_2$ represents H, and X represents nitrogen or a methine group.

29. The method of claim 3 wherein $R_1$ represents a polyolefin polymer-bound group; $R_2$ represents H, and X represents nitrogen or a methine group.

* * * * *

UNITED STATES PATENT AND TRADEMARK OFFICE
CERTIFICATE OF CORRECTION

PATENT NO. : 6,432,396 B1
DATED : August 13, 2002
INVENTOR(S) : Landgrebe Kevin D.

It is certified that error appears in the above-identified patent and that said Letters Patent is hereby corrected as shown below:

Column 7,
Line 61, delete "aLkylamino" and insert in place thereof -- alkylamino --.

Column 8,
Line 15, delete "dinerization" and insert in place thereof -- dimerization --.

Column 16,
Line 64, delete "ContaininE" and insert in place thereof -- Containing --.

Column 17,
Line 11, delete "Polyproivlene-Bound" and insert in place thereof -- Polypropylene-Bound --.
Line 26, delete "10% HN03" and insert in place thereof -- 10% $HNO_3$ --.

Column 18,
Line 38, delete "acetate 1N,N-dimethyl" and insert in place thereof
-- acetate/N,N-dimethyl --.
Line 52, delete "(MSV-1)" and insert in place thereof -- (HSV-1) --.

Column 20,
Line 17, delete "[DPD]=10 4 M" and insert in place thereof -- [DPD]=$10^{-4}$ M--.

Column 21,
Line 10, delete "retained" and insert in place thereof -- methine --.
Line 58, delete "grain" and insert in place thereof -- gram --.

Signed and Sealed this

Thirtieth Day of September, 2003

JAMES E. ROGAN
*Director of the United States Patent and Trademark Office*